United States Patent [19]

Ryan

[11] Plant 4,194

[45] Jan. 17, 1978

[54] IMPATIENS PLANT—HOPI

[76] Inventor: John J. Ryan, 39877 Sundale Drive, Fremont, Calif. 94538

[21] Appl. No.: 782,283

[22] Filed: Mar. 28, 1977

[51] Int. Cl.[2] ..... A01H 5/00
[52] U.S. Cl. ..... Plt./68
[58] Field of Search ..... Pts./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Hopi, and discovered by me in commercial greenhouses in Fremont, Calif. Hopi is closest in characteristics to Longwood's Stoplight but is particularly characterized by short internodes; a small, abundant, very bright red-orange flower; a glossy, bright-green spreading foliage; quite sodium sensitive; yet excellent breaking action making a very full basket.

1 Drawing Figure

BACKGROUND OF THE INVENTION

The present new variety (seedling 76-30-1) was discovered by me in a commercial greenhouse in Fremont, Calif. as a result of the cross pollination of unpatented pistol parent 75-14 and unpatented pollen parent 75-7.

Asexual reproduction of my new cultivar by terminal or stem cuttings grown in hanging baskets in a plastic (polyethylene) greenhouse in Fremont, Calif. under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Hopi is closest in characteristics to Longwood's Stoplight. The following outstanding characteristics of Hopi distinguish it from Longwood's Stoplight:

1. Plant habit of Hopi is spreading; Stoplight is upright.
2. Hopi will flower sooner and produce more flowers in a given time.
3. It has extremely good breaking action, producing many cuttings and completely fills a basket.
4. The flower color of Hopi is red-orange; wheras Stoplight is red.
5. Hopi's flower is about ½ to ¾ the size of Stoplight.
6. The glossy, bright green foliage of Hopi is lighter in color, yet brighter than Stoplight.

DESCRIPTION OF THE PHOTOGRAPH

The accompanying colored photograph illustrates the overall appearance of the cultivar Hopi showing the colors as true as reasonably possible for this type of colored reproduction. However, under low light and cool temperatures the flower darkens, becoming more red than red-orange.

DETAILED DESCRIPTION

The following detailed description of Hopi is based on observations made of the new cultivar on Jan. 13, 1977.

PLANT

Name: Hopi.

Origin: Seedling 76-30-1 of the cross pollination of unpatented pistil parent 75-14 and unpatented pollen parent 75-7.
Height to flowering: ~ 30 cm.
Growth: Fast.
Type of cuttings: Terminal or stem.
Rooting time: Typical, 10–14 days.
Rooting habit: Fast, dendritic.

FOLIAGE

Arrangement: Lower leaves opposite (usually one set), upper foliage of any shoot whorls of 3–5 (mostly 5's).
Shape: Elliptic (slightly variable).
Tip: Broadly to abruptly accuminate.
Base: Attenuate.
Margin: Ciliate at base to serrulate at tip.
Venation: Pinnate.
Size: Blade and petiole 13 to 15 cm., length of blade 9 to 10 cm., width of blade at widest point 3.5 to 4 cm.
Surface:
*Smoothness.*—smooth with occasional slight cupping of leaf end.
*Texture.*—Glabrous, typically waxy.
Variegation: None.
Color:
*Petiole.*—53C lower, 54B upper.
*Veins.*—53D lower, 145D upper.
*Leaf.*—upper 137C; lower 139D.

STEM

Color: 53C.
Internode:
*Length.*—Short to moderate.
*Size.*—Small to moderate.
Node expanded (relative to internode): Sightly expanded.
Breaking action: Excellent.

FLOWER

Form: Typical
Borne: End of branches, terminal.
Blooming habit:

| | |
|---|---|
| Relative number: above average<br>Time to flowering: average | heavily dependent on quantity and type of fertilizer |

*Longevity.*—5 days (heavily dependent on temperature).

Size of mature flower: First flower on a plant may be small.

*Length.*—4.5 to 5 cm.

*Width.*—4.0 to 4.5 cm.

*Spur.*—4.0 to 5.0 cm.

Color: Becomes more orange under high light.

*Eye.*—45B.

| | |
|---|---|
| Middle<br>Edge | 44B |

*Pedicel.*—53B - 53C.

REPRODUCTIVE ORGANS

Stamen:

| | |
|---|---|
| Anthers<br>Filaments | typical in form but smaller; fused hood over pistil |

*Pollen.*—Color: 158b; Abundance: Typical, plenty.

Pistils:

| | |
|---|---|
| Style<br>Ovaries | typical form, but smaller |

OTHER CHARACTERISTICS

Diseases: Hopi is no more susceptible than other Impatiens varieties to most soft rots.

High amonia fertilization and/or high temperatures may reduce the number of flowers developed in the cultivar Hopi.

I claim:

1. A new and distinct form of Impatiens plant as described and illustrated, known by the cultivar name Hopi, and particularly characterized by short internodes, a small abundant very bright red-orange flower, a glossy bright green spreading foliage; quite sodium sensitive; yet excellent breaking action making a very full basket.

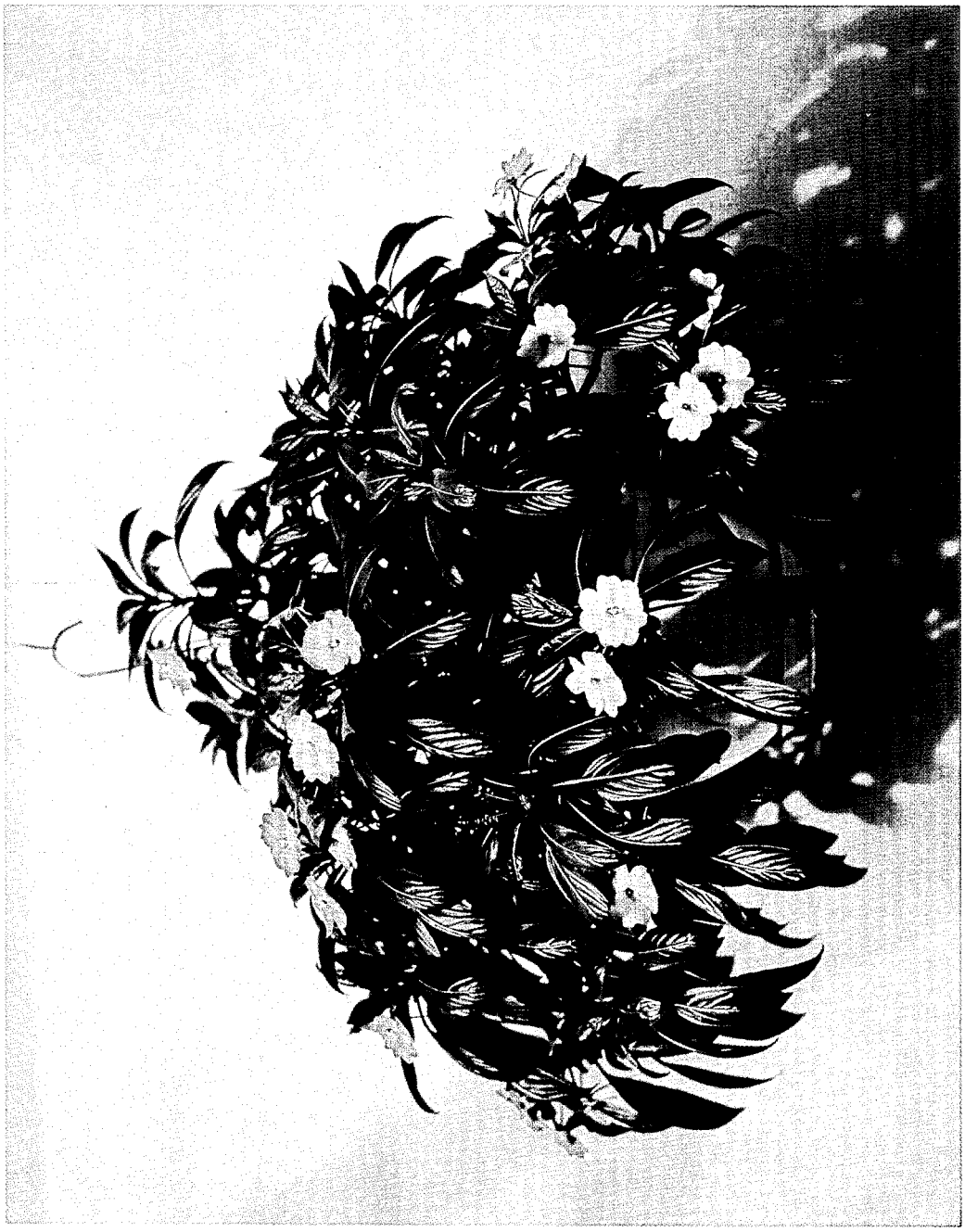

* * * * *